United States Patent
Arce

(10) Patent No.: US 10,688,106 B2
(45) Date of Patent: *Jun. 23, 2020

(54) OXYTOCIN RECEPTOR ANTAGONIST THERAPY IN THE LUTEAL PHASE FOR IMPLANTATION AND PREGNANCY IN WOMEN UNDERGOING ASSISTED REPRODUCTIVE TECHNOLOGIES

(71) Applicant: Ferring B.V., Hoofddorp (NL)

(72) Inventor: Joan-Carles Arce, Dragor (DK)

(73) Assignee: FERRING B.V., Hoofddorp (NL)

( * ) Notice: Subject to any disclaimer, the term of this patent is extended or adjusted under 35 U.S.C. 154(b) by 277 days.

This patent is subject to a terminal disclaimer.

(21) Appl. No.: 15/538,639

(22) PCT Filed: Dec. 21, 2015

(86) PCT No.: PCT/NL2015/050893
§ 371 (c)(1),
(2) Date: Jun. 21, 2017

(87) PCT Pub. No.: WO2016/105190
PCT Pub. Date: Jun. 30, 2016

(65) Prior Publication Data
US 2017/0348325 A1  Dec. 7, 2017

Related U.S. Application Data

(63) Continuation of application No. 14/643,307, filed on Mar. 10, 2015, now Pat. No. 9,579,305.

(30) Foreign Application Priority Data

Dec. 22, 2014 (EP) .................... 14199709

(51) Int. Cl.
*A61K 31/57* (2006.01)
*A61K 31/404* (2006.01)
(Continued)

(52) U.S. Cl.
CPC ............ *A61K 31/57* (2013.01); *A61B 17/435* (2013.01); *A61K 9/0019* (2013.01);
(Continued)

(58) Field of Classification Search
CPC ................... A61B 17/425–435; A61K 31/404
See application file for complete search history.

(56) References Cited

U.S. PATENT DOCUMENTS 6,143,722 A   11/2000  Melin et al.
6,605,468 B1   8/2003  Robertson et al.
(Continued)

FOREIGN PATENT DOCUMENTS

WO  WO-98/23636 A1  6/1998
WO  WO-2004/020414 A1  3/2004
(Continued)

OTHER PUBLICATIONS

Fisk N. and Atun R. Market Failure and the Poverty of New Drugs in Maternal Health. PLoS Medicine vol. 5, issue 1, p. 0022-0028, Jan. 2008 (Year: 2008).*

(Continued)

*Primary Examiner* — Catherine B Kuhlman
(74) *Attorney, Agent, or Firm* — Brenda H. Jarrell; Rolando Medina; Choate, Hall & Stewart, LLP

(57) ABSTRACT

The present invention relates to the use of an oxytocin receptor antagonist in females undergoing embryo transfer as part of an assisted reproductive technology. In particular, methods are provided for increasing ongoing implantation rate, increasing ongoing pregnancy rate, increasing clinical pregnancy rate, and/or increasing live birth rate in a female subject undergoing embryo transfer. Specifically, the antagonists are released in the luteal phase when the endometrium is receptive for embryo implantation and/or when the embryo has reached the blastocyst-stage.

18 Claims, 4 Drawing Sheets

(51) Int. Cl.

| | |
|---|---|
| A61B 17/435 | (2006.01) |
| A61K 38/095 | (2019.01) |
| A61K 38/12 | (2006.01) |
| A61K 45/06 | (2006.01) |
| A61K 31/4045 | (2006.01) |
| A61K 31/565 | (2006.01) |
| A61K 9/00 | (2006.01) |

(52) U.S. Cl.
CPC .......... *A61K 9/0034* (2013.01); *A61K 31/404* (2013.01); *A61K 31/4045* (2013.01); *A61K 31/565* (2013.01); *A61K 38/095* (2019.01); *A61K 38/12* (2013.01); *A61K 45/06* (2013.01)

(56) References Cited

U.S. PATENT DOCUMENTS

| | | | |
|---|---|---|---|
| 7,091,314 | B2 | 8/2006 | Wisniewski et al. |
| 7,304,181 | B2 | 12/2007 | Wisniewski et al. |
| 7,816,489 | B2 | 10/2010 | Wisniewski et al. |
| 9,579,305 | B2 | 2/2017 | Arce |
| 10,183,029 | B2 | 1/2019 | Arce |
| 2005/0050489 | A1 | 3/2005 | Chen et al. |
| 2006/0069031 | A1 | 3/2006 | Loumaye |
| 2008/0234203 | A1 | 9/2008 | Reinheimer et al. |
| 2008/0318847 | A1* | 12/2008 | Kuczynski ......... A61K 31/4025 514/1.1 |
| 2012/0040849 | A1 | 2/2012 | Simon Valles et al. |
| 2012/0252119 | A1 | 10/2012 | Gilchrist et al. |
| 2014/0017717 | A1 | 1/2014 | Loewke et al. |
| 2014/0134632 | A1 | 5/2014 | Hamamah |
| 2016/0175283 | A1 | 6/2016 | Arce |
| 2017/0189415 | A1 | 7/2017 | Arce |

FOREIGN PATENT DOCUMENTS

| | | |
|---|---|---|
| WO | WO-2005/028454 A1 | 3/2005 |
| WO | WO-2006/121362 A2 | 11/2006 |
| WO | WO-2013/078312 A1 | 5/2013 |
| WO | WO-2014/080032 A1 | 5/2014 |

OTHER PUBLICATIONS

ObsEva, ClinicalTrials.gov. OBE001 Phase 2 Dose-Finding Study Versus Placebo in Women Undergoing Embryo Transfer in the Context of IVF-ICSI (Implant). Dec. 8, 2014. https://clinicaltrials.gov/ct2/show/study/NCT02310802 (Year: 2014).*

Ayoubi, J.M. et al., Comparison of changes in uterine contraction frequency after ovulation in the menstrual cycle and in in vitro fertilization cycles, Fertil. Steril., 79: 1101-1105 (2003).

Bergh, P.A. and, Navot D. The impact of embryonic development and endometrial maturity on the timing of implantation, Fertil. Steril., 58: 537-542 (1992).

Bernabeu, R. et al., Indomethacin effect on implantation rates in oocyte recipients, Hum. Reprod., 21: 364-369 (2006).

Blockeel, C. et al. Effects of barusiban and atosiban on frequency of uterine contractions in the luteal phase after stimulation: a randomised placebo-controlled trial, Selected Oral Communication Session, Section 17: Implantation, Abstracts of the 25th Annual Meeting of ESHRE, Amsterdam, the Netherlands, 15:15-16:30 (Jun. 29, 2009).

Bulleti, C. and de Ziegler, D. et al., Uterine contractility and embryo implantation, Curr. Opin. Obstet. Gynecol., 17:265-276 (2005).

Chou, P-Y. et al., Use of an oxytocin antagonist in in-vitro fertilization-embryo transfer for women with repeated implantation failure: A retrospective study, Taiwanese Journal of Obstetrics & Gynecology, 50: 136-140 (2011).

ClinicalTrials.gov archive, A Phase 2, Double-blind, Dose-finding, Placebo-controlled Study to Assess the Safety and Efficacy of a Single Oral Administration of OBE001 to Improve Embryo Implantation Following IVF or ICSI, Clinical Trials Identifier: NCT02310802 (Dec. 7, 2014). URL: https://clinicaltrials.gov/archive/NCT02310802/2014_12_07 [Retrieved Aug. 7, 2015].

Decleer, W. et al., The role of oxytocin antagonists in repeated implantation failure, Facts, Views & Vision in ObGyn., 4(4): 227-229 (2012).

Fanchin, R. et al., Effects of vaginal progesterone administration on uterine contractility at the time of embryo transfer, Fertil. Steril., 75: 1136-1140 (2001).

Fanchin, R. et al., Uterine contractions at the time of embryo transfer alter pregnancy rates after in-vitro fertilization, Hum. Reprod., 13: 1968-1974 (1998).

Ferring Pharmaceuticals, Effect of Oxytocin Antagonist on reduction of uterine contractions, Clinical Trials, gov identifier NCT01043120, retrieved May 1, 2015, last updated Apr. 16, 2013.

Fuchs, A. R. et al., Oxytocin and vasopressin receptors in human and uterine myomas during menstrual cycle and early pregnancy, Hum. Reprod. Update, 4: 594-604 (1998).

Gardner, D. K. et al, A prospective randomized trial of blastocyst culture and transfer in in-vitro fertilization, Human Reproduction, 13(12): 3434-3440 (1998).

Gardner, O.K. et. al., Blastocyst score affects implantation and pregnancy outcome: towards a single blastocyst transfer, Fertility and Sterility, 73(6): 1155-1158 (2000).

Groenewoud, E. et al., What is the optimal means of preparing the endometrium in frozen-thawed embryo transfer cycles? A systematic review and meta-analysis, Human Reproduction Update, 19(5): 458-470 (2013).

Killick S.R., Ultrasound and the receptivity of the myometrium, RBM Online, 15: 63-67 (2007).

Kim, C.H. et al., Administration of oxytocin antagonist improves the implantation rates in patients with repeated failure of IVF/ICSI treatment, Hum. Reprod., 23 (Suppl. 1): i124 (2008).

Koot, Y.E.M. and Macklon, N.S., Embryo implantation: biology, evaluation, and enhancement, Curr. Opin. Obstet. Gynecol., 25: 274-279 (2013).

Kuc, P., Optimal Environment for the Implantation of Human Embryo, The Human Embryo, Dr. Shigehito Yamada (Ed.), In Tech (2012). URL: http://www.intechopen.com/books/the-human-embryo/optimal-environmentfor-the-implantation-of-human-embryo.

Lan, V.T. et al., Atosiban improves implantation and pregnancy rates in patients with repeated implantation failure, RBM Online, 25: 254-260 (2012).

Lesny, P. et al., Embryo transfer—can we learn anything new from the observation of junctional zone contractions? Hum Reprod., 13: 1540-1546 (1998).

Liang, Y.L. et al., Oxytocin antagonist for repeated implantation failure and delay of delivery, Taiwan. J. Obstet. Gynecol., 48: 314-316 (2009).

Makrigiannakis, A. and Minas, V., Mechanisms of implantation, RBM Online, 14: 102-109 (2006).

Merkus, F. W. H. M. et al., Absorption enhancers in nasal drug delivery: efficacy and safety, J. Controlled Release, 24: 201-208 (1993).

Moon, H.S. et al.,Treatment with piroxicam before embryo transfer increases the pregnancy rate after in vitro fertilization and embryo transfer, Fertil. Steril., 82: 816-820 (2004).

Moraloglu, O. et al., Treatment with oxytocin antagonists before embryo transfer may increase implantation rates after IVF, RBM Online, 21: 338-343 (2010).

NG, E.H. et al., A randomized double blind comparison of atosiban in patients undergoing IVF treatment. Hum. Reprod., 29: 2687-2694 (2014).

Papanikolaou, E.G. et al., Live birth rates after transfer of equal number of blastocysts or cleavage-stage embryos in IVF. A systematic review and meta-analysis, Hum. Reprod., 23: 91-99 (2008).

Pierzynski, P. et al., Oxytocin antagonists may improve infertility treatment, Fertil Steril., 88: e19-e22 (2007).

Pierzynski, P., Oxytocin and vasopressin V1 A receptors as new therapeutic targets in assisted reproduction, Reproductive BioMedicine Online, 22: 9-16 (2011).

Prados, F.J. et al., The cleavage stage embryo, Human Reproduction, 27:50-71 (2012).

(56) References Cited

OTHER PUBLICATIONS

Reinheimer, T. et al, Barusiban, an effective long-term treatment of oxytocin-induced preterm labor in nonhuman primates, Biology of Reproduction, 75(5): 809-14 (2006).
Richter, O.N. et al., Contractile reactivity of human myometrium in isolated non-pregnant uteri, Hum. Reprod., 21: 36-45 (2006).
Schoolcraft, W.B. et al., Embryo transfer: techniques and variables affecting success, Fertil. Steril., 76: 863-870 (2001).
Shukovski, L. et al., Circulating immunoreactive oxytocin during the human menstrual cycle comes from the pituitary and is estradiol dependent, J. Clin. Endocrinol. Metab., 68: 455-460 (1989).
Simón, C. et al., Paracrine regulators of implantation, Clin. Obstet. Gynaecol., 14: 815-826 (2000).
Strowitzki, T. et al., The human endometrium as a fertility-determining factor, Hum. Reprod. Update, 12: 617-630 (2006).
Vrachnis, N. et al., The ocytocin-ocytocin receptor system and its antagonists as tocolytic agents, International Journal of Endocrinology, 2011(Article ID 353546): 1-8 (2011).
Zhu, L. et al., Uterine peristalsis before embryo transfer affects the chance of clinical pregnancy in fresh and frozen-thawed embryo transfer cycles, Hum. Reprod., 29: 1238-1243 (2014).
Press Release, Obseva Announces That Nolasiban Implant 4 Study Did Not Meet Primary Endpoint—Company to Discontinue Current Nolasiban IVF Program, Obseva Obsetrics & Beyond, Nov. 7, 2019. https://www.obseva.com/pressrelease-detail/?pr=2714.

\* cited by examiner

Figure 2

| | Barusiban | Placebo | Odds ratio [95% CI] | p-value |
|---|---|---|---|---|
| Ongoing implantation rate Day 3 + Day 5 | 27.1% | 28.2% | 1.1 [0.7; 1.8] | 0.6960 |

| | Odds ratio [95% CI] | p-value |
|---|---|---|
| Ongoing implantation rate Barusiban vs placebo | | |
| Day 3 | 0.6 [0.3; 1.2] | 0.1509 |
| Day 5 | 2.3 [1.1; 4.7] | 0.0270 |

Analyses adjusted for site, primary reason for infertility and embryo/blastocyst quality

OXYTOCIN RECEPTOR ANTAGONIST THERAPY IN THE LUTEAL PHASE FOR IMPLANTATION AND PREGNANCY IN WOMEN UNDERGOING ASSISTED REPRODUCTIVE TECHNOLOGIES

CROSS REFERENCE TO RELATED APPLICATIONS

The present application is the National Stage of International Application No. PCT/NL15/50893, filed Dec. 21, 2015 which claims the benefit of EP Application No. 14199709.8, filed Dec. 22, 2014, and U.S. application Ser. No. 14/643,307 filed 10 Mar. 2015, the contents of each of which are herein incorporated by reference in their entirety.

FIELD OF THE INVENTION

The present invention relates to the use of an oxytocin receptor antagonist in females undergoing embryo transfer as part of an assisted reproductive technology. In particular, methods are provided for increasing ongoing implantation rate, increasing ongoing pregnancy rate, increasing clinical pregnancy rate, and/or increasing live birth rate in a female subject undergoing embryo transfer. Specifically, the antagonists are released in the luteal phase when the endometrium is receptive for embryo implantation and/or when the embryo has reached the blastocyst-stage.

BACKGROUND OF THE INVENTION

In vitro fertilization (IVF) is a method for establishing pregnancy in a female subject. The procedure typically involves ovarian stimulation with one or various hormones, mainly follicle-stimulating hormone (FSH), and human chorionic gonadotropin (hCG) is usually administered to trigger final follicular maturation. Oocyte retrieval takes place generally 2 days (around 36 h) after hCG administration. The ooctyes are then fertilized in vitro, cultured for several days, and are transferred into the uterus. IVF also encompasses the transfer of embryos originating from the eggs of a first female (the donor) into a second female (the gestational carrier). Embryos may be placed in frozen storage and transferred (i.e., frozen embryo transfer) after several months or even years.

Improving the implantation rate of transferred embryos is one of the major challenges in assisted reproductive technologies (ART) treatment. Approximately only one-third of the transferred embryos implant in women undergoing controlled ovarian stimulation for IVF/intracytoplasmic sperm injection (ICSI). Implantation and pregnancy rates are influenced by multiple factors related to the age and other characteristics of the patient, the magnitude of the response to ovarian stimulation, the quality of the embryos obtained, the endometrial receptivity as well as the actual transfer procedure.

Uterine contractility is considered a potentially important factor affecting implantation and pregnancy rates in IVF/ICSI cycles (Fanchin et al. 1998; Schoolcraft et al. 2001; Bulleti and de Ziegler 2005). A high frequency of uterine contractions at the time of transfer appears to have a negative impact on outcome, possibly by expelling the embryos in the uterine cavity or by displacing the embryos and thereby reducing implantation and pregnancy rates.

Observational data indicated a decrease in clinical pregnancy rates with increasing frequency of contractions at the time of cleavage-stage embryo transfer at hCG+4 days (i.e., four days after hCG administration, corresponding to day 2 post-retrieval of oocytes) (Fanchin et al. 1998). A prospective controlled study also observed that patients with a higher frequency of uterine contractions on the day of cleavage-stage embryo transfer (day 3 post-retrieval) had lower pregnancy rates than patients with lower frequency of uterine contractions at the time of transfer (Zhu et al. 2014).

Uterine contractility in controlled ovarian stimulation cycles has been compared to normal menstrual cycles (Ayoubi et al. 2003). The frequency of uterine contractions was found to be similar between the timepoint of hCG administration in a controlled ovarian stimulation cycle and at the time of luteinizing hormone (LH) surge in a natural cycle. In the luteal phase, the frequency of uterine contractions was higher at hCG+4 days (corresponding to day 2 post-retrieval) in a controlled ovarian stimulation cycle compared to at LH+4 days (i.e., four days after LH surge) in a natural cycle (Ayoubi et al. 2003). However, the frequency of uterine contractions at LH+6 days and hCG+6 days (corresponding to day 4 post-retrieval) was not different and in both situations was low, indicating identical level of uterine quiescence at that time point in controlled ovarian stimulation and natural cycles (Ayoubi et al. 2003). In another study, uterine contractility was assessed at the day of hCG administration, hCG+4 days (corresponding to day 2 post-retrieval) and hCG+7 days (corresponding to day 5 post-retrieval) in women undergoing a controlled ovarian stimulation cycle (Fanchin et al. 2001). The frequency of uterine contractions was highest at the day of hCG administration, decreased slightly during the early luteal phase as assessed at hCG+4 days, and reached nearly quiescent status at hCG+7 days (corresponding to day 5 post-retrieval). Another study reported a decrease in the number of junctional zone contractions in oocyte donors in the early luteal phase from day 2 to day 3 and also to day 4 post-retrieval (Lenny et al. 1999). Similarly, evaluation of uterine contractility in oocyte donors who had undergone controlled ovarian stimulation and received exogenous progesterone luteal phase supplementation indicated that there was a significant decrease in the frequency of uterine contractions from day 2 post-retrieval to day 5 post-retrieval (Blockeel et al. 2009).

The highest level of uterine contractility is at the end of controlled ovarian stimulation (day of hCG administration) and has been attributed to the high serum estradiol and low serum progesterone concentrations at that time point. The decrease in uterine contractility during the luteal phase is believed to be the result of the exposure to endogenous progesterone caused by the corpus luteum function in response to the hCG administration as well as exogenous progesterone luteal supplementation used in IVF/ICSI cycles. Although progesterone supplementation is used for luteal phase support in IVF/ICSI patients and can reduce uterine contractility, there is elevated uterine activity during the early luteal phase (day 2 or 3 post-retrieval) when transfer of cleavage-stage embryos is performed.

As uterine contractility is elevated during the early luteal phase (day 2 or 3 post-retrieval) when transfer of cleavage-stage embryos is performed, investigations assessing the impact of different interventions on uterine contractility for improving implantation have been conducted in the early luteal phase (day 2 and 3 post-retrieval transfer; hCG+4 days). Randomized controlled trials (Moon et al. 2004; Bernabeu et al 2006; Kim et al. 2008; Ng et al. 2014), quasi-randomized controlled trials (Moraloglu et al. 2010), retrospective studies in fresh and frozen embryo replacement cycles (Chou et al. 2011; Lan et al. 2012), or case studies in fresh and frozen embryo replacement cycles (Pierzynski et al. 2007; Liang et al 2009) reporting findings with compounds reducing uterine contractility, like atosiban (Kim et al 2008; Moraloglu et al. 2010; Ng et al. 2014), indomethacin (Bernabeu et al. 2006) and piroxicam (Moon et al. 2004) have been all conducted on day 2 or 3 post-retrieval, i.e., at the time of cleavage-stage embryo transfer.

A recent randomized controlled trial (Ng et al. 2014) compared the treatment outcome after administration of atosiban or placebo in IVF/ICSI patients followed by cleavage-stage embryo transfer on day 2 or day 3 post-retrieval. This large study was designed to determine whether the anecdotal evidence found in the previous smaller studies could be confirmed. This adequately-designed, large (N=800), double-blind, randomized, controlled trial found no significant increase in implantation or live birth rates with atosiban compared to placebo, as illustrated by live birth rates of 39.8% versus 38.0%, respectively (Ng et al. 2014). Atosiban administration on day 2 or day 3 post-retrieval therefore does not significantly increase implantation or live birth rates.

Consequently, improving implantation of transferred embryos remains one of the major challenges in assisted reproductive technologies (ART) treatment. It is an object of the present disclosure to improve implantation rates, thereby increasing pregnancy rates and live birth rates.

SUMMARY OF THE INVENTION

One aspect of the disclosure provides an oxytocin receptor antagonist for use in increasing ongoing implantation rate, increasing ongoing pregnancy rate, increasing clinical pregnancy rate, and/or increasing live birth rate, relative to control, in a female subject undergoing embryo transfer as part of an assisted reproductive technology, wherein the antagonist is provided to the female such that the effect of the antagonist is present when the female is in (or otherwise overlaps with) the receptive endometrium stage and/or when the effect of the antagonist coincides with the embryo reaching the blastocyst-stage. Preferably, the antagonist is provided such that it is released in the receptive endometrium stage and/or when the embryo has reached the blastocyst-stage. Preferably, the antagonist is administered when the female is in the receptive endometrium stage and/or when the embryo has reached the blastocyst-stage. In certain embodiments, the antagonist is formulated for immediate release. In other embodiments, the antagonist is formulated as a sustained or delayed release formulation, such as a depot, and is administered prior to the receptive endometrium stage and/or when the embryo is still in cleavage stage such that the antagonist is released or continues to be released once the receptive endometrium stage is reached and/or the embryo has reached the blastocyst stage. Preferably, the antagonist is provided such that a therapeutically effective amount of the antagonist is present when the female is in (or otherwise overlaps with) the receptive endometrium stage and/or when the effect of the antagonist coincides with the embryo reaching the blastocyst-stage.

In preferred embodiments, the receptive endometrium stage corresponds to:

a) between LH+6 days and LH+9 days, preferably between LH+6 days and LH+8 days, most preferably on day LH+7 of a natural ovulation cycle;

b) between hCG+6 days and hCG+9 days, preferably between hCG+6 days and hCG+8 days; most preferably on day hCG+7 of an induced ovulation cycle;

c) between day 4 and day 7, preferably between day 4 and day 6, more preferably on day 5 or 6, most preferably on day 5, of luteal phase support, wherein luteal phase support begins the day following oocyte retrieval in an IVF cycle, preferably wherein the female has undergone ovarian stimulation; or d) between day 4 to day 9, preferably between day 5 to day 7, more preferably on day 5 or day 6 of luteal phase support, preferably in preparation for frozen embryo transfer or third party IVF, and preferably wherein luteal support begins after the endometrium is primed for at least 6 days with exogenous oestrogen.

Preferably, luteal phase support comprises supplementation with progesterone, human chorionic gonadotropin, estradiol and progesterone, progestins and/or gonadatropin releasing hormone (GnRH) agonists.

Accordingly, the disclosure provides oxytocin receptor antagonists which can be used to prepare medicaments for increasing ongoing implantation rate, increasing ongoing pregnancy rate, increasing clinical pregnancy rate, and/or increasing live birth rate, in a female subject undergoing embryo transfer as part of an assisted reproductive technology. Also encompassed by the disclosure are uses of oxytocin receptor antagonist for the preparation of a medicament for use in a female undergoing transfer of a blastocyst-stage embryo. Preferably a medicament is administered such that its effect overlaps with the receptive endometrium stage and/or when the embryo has reached the blastocyst-stage. Preferably, an antagonist in a medicament is released in the female when the female is in the receptive endometrium stage and/or when the embryo has reached the blastocyst-stage. Preferably, an antagonist is provided such that a therapeutically effective amount of the antagonist is present when the female is in (or otherwise overlaps with) the receptive endometrium stage and/or when the effect of the antagonist coincides with the embryo reaching the blastocyst-stage.

The disclosure further encompasses methods for increasing ongoing implantation rate, increasing ongoing pregnancy rate, increasing clinical pregnancy rate, and/or increasing live birth rate, in a female subject undergoing embryo transfer as part of an assisted reproductive technology, comprising administering to the female an oxytocin receptor antagonist such that the effect of the antagonist overlaps with the receptive endometrium stage and/or when the embryo (e.g., transferred embryo) has reached the blastocyst-stage. Preferably, methods are provided for increasing ongoing implantation rate, increasing ongoing pregnancy rate, increasing clinical pregnancy rate, and/or increasing live birth rate in a female, said method comprising administering to the female prior to and/or following embryo transfer an oxytocin receptor antagonist such that a therapeutically effective amount of the antagonist is present during at least a portion of the receptive endometrium stage of the female and/or during at least a portion of the blastocyst-stage of a transferred embryo in the female, thereby increasing ongoing implantation rate, increasing ongoing pregnancy rate, increasing clinical pregnancy rate, and/or increasing live birth rate relative to a control. In preferred embodiments, the methods further comprise transferring an embryo into the uterus, the uterine cavity or the fallopian tubes of a female, preferably wherein a blastocyst-stage embryo is transferred.

The disclosure further provides methods of implanting an embryo in a female subject, comprising transferring an embryo into the uterus, the uterine cavity or the fallopian tubes of a female and administering to the female an oxytocin receptor antagonist such that the effect of the antagonist overlaps with the blastocyst-stage of the embryo and/or the female is in the receptive endometrium stage. Preferably, an antagonist is provided such that a therapeutically effective amount of the antagonist is present when the female is in (or otherwise overlaps with) the receptive endometrium stage and/or when the effect of the antagonist coincides with the embryo reaching the blastocyst-stage.

Methods are also provided for implanting an embryo in a female subject, said method comprising transferring an embryo into the uterus, the uterine cavity or the fallopian tubes of a female and administering to the female an oxytocin receptor antagonist such that a therapeutically effective amount of the antagonist is present in the female during at least a portion of the receptive endometrium stage of the female and/or during at least a portion of the blastocyst-stage of the transferred embryo in the female In preferred embodiments, the female is undergoing transfer of a blastocyst-stage embryo and the antagonist is administered to the female such that the antagonist is released to the female on the same day that the embryo is transferred. Preferably, the antagonist is administered between 2 hours prior to and 2 hours post embryo transfer (for example, in an immediate release formulation), preferably wherein the antagonist is administered twice, preferably wherein the first administration occurs around 45 minutes prior to embryo transfer and the second administration occurs around 60 minutes after the first administration. Preferably, a blastocyst-stage embryo has an expansion and hatching status of 3, 4, 5, or 6, more preferably wherein the blastocyst-stage embryo is a day 5 post-insemination embryo.

In preferred embodiments, the female is undergoing transfer of a cleavage-stage embryo and the antagonist is administered to the female such that the antagonist is released two or three days after the embryo is transferred. Preferably, a cleavage-stage embryo has at least 6 blastomeres and fragmentation of 20% or less, preferably wherein the cleavage-stage embryo is a day 2 or day 3 post-fertilization embryo.

In preferred embodiments, the antagonist is a selective oxytocin receptor antagonist or an vasopressin/oxytocin receptor antagonist. More preferably, the antagonist is a selective oxytocin receptor antagonist.

Preferably, the antagonist is barusiban. Preferably, barusiban is provided subcutaneously. Preferably, between 30-80 mg, more preferably 50 mg of barusiban is administered. In some embodiments, the female is undergoing transfer of a blastocyst-stage embryo and barusiban is administered to the female as a depot prior to the day of embryo transfer. Preferably, the female is undergoing transfer of a blastocyst-stage embryo and barusiban is administered to the female on the same day as embryo transfer. Preferably, 40 mg barusiban is administered subcutaneously about 15, 30, 45, 60, or 75 minutes (e.g., 45 minutes) prior to blastocyst stage embryo transfer and 10 mg barusiban is administered subcutaneously about 15, 30, 45, 60, or 75 minutes (e.g., 60 minutes) after the first administration.

BRIEF DESCRIPTION OF THE DRAWINGS

FIG. 2 depicts odds ratio for ongoing implantation rate by day of transfer for (BASIC) clinical trial.

DETAILED DESCRIPTION OF THE DISCLOSED EMBODIMENTS

Figure 1A:
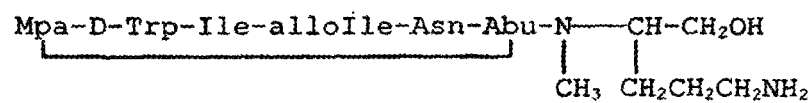
FIGS. 1A and 1B depict examples of oxytocin receptor antagonists.
Figure 1A:
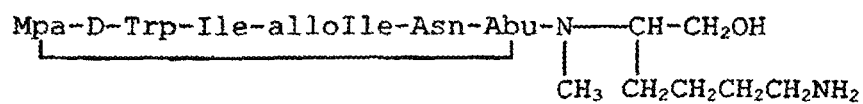
Figure 1A:
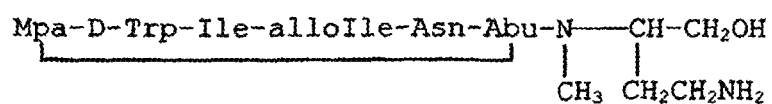
Figure 1A:
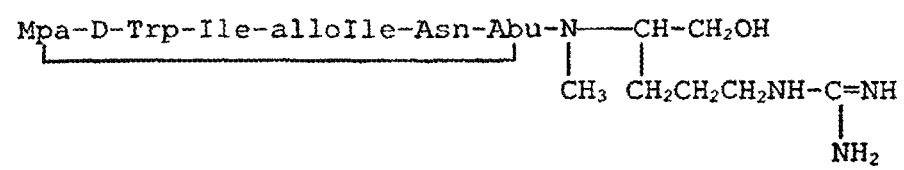
Figure 1A:
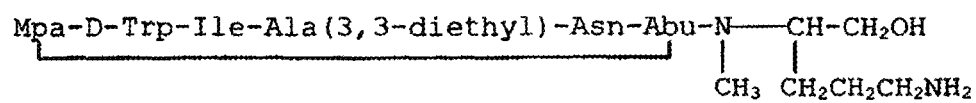
Figure 1B:
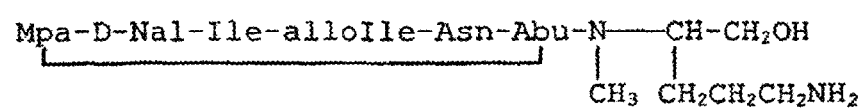
Figure 1B:
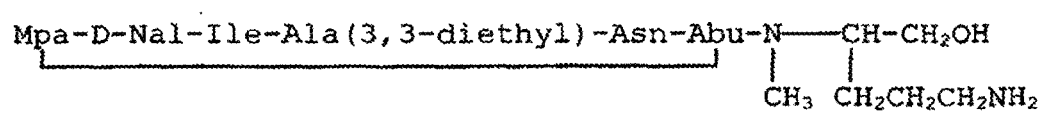
Figure 1B:
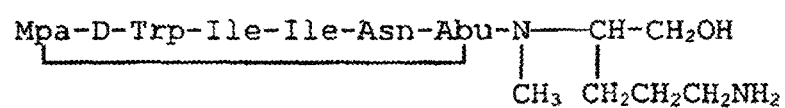
Figure 1B:
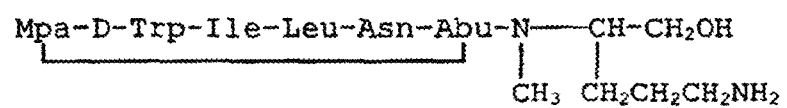
Figure 1B:
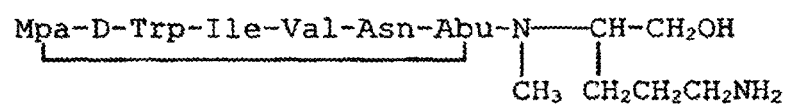
Figure 1B:
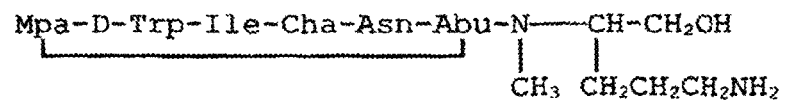

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article. By way of example, "an element" means one element or more than one element.

The word "approximately" or "about" when used in association with a numerical value (approximately 10, about 10) preferably means that the value may be the given value of 10 more or less 1% of the value.

When referring herein to a range, such as, e.g., a range of days, the range includes both end points. For example, day LH+6 to day LH+9 encompasses day LH+6, day LH+7, day LH+8, and day LH+9.

As used herein, the term "embryo" refers to a zygote up to eight weeks after fertilization. "Embryo transfer" is the procedure in which one or more embryos are placed into the uterus, uterine cavity, or fallopian tubes of a female.

As used herein, a female subject is a mammal which includes humans; companion animals, e.g., dogs and cats; domestic livestock animals, such as pigs, horses, donkeys, goats, sheep, llamas; as well as rare and threatened species. Preferably, the subject is human.

Assisted reproductive technology (ART) refers to methods for achieving pregnancy using artificial means. Preferably, ART refers to methods in which an in vitro fertilized embryo is transferred into a female subject, for example using IVF/ICSI.

"Fresh embryo transfer" refers to the transfer of an embryo without first freezing the embryo.

Generally, the natural ovulation cycle ranges from 21 to 35 days, with the average length being 28 days. The first part of the cycle is referred to as the follicular phase in which the ovarian follicles mature. Ovulation follows by which a mature egg is released into the oviduct. The luteal phase refers to a phase of the ovulation cycle beginning with the formation of the corpus luteum at LH+1 and finishing the day before the first day of menstruation.

"Ongoing implantation rate" as used herein refers to the number of intrauterine viable fetuses 10-11 weeks after transfer divided by number of embryos/blastocysts transferred. Preferably, the administration of an oxytocin receptor antagonist as disclosed herein increases the ongoing implantation rate by at least 5%, more preferably by at least 10% and most preferred by at least 20%.

"Ongoing pregnancy rate" as used herein refers to a pregnancy with at least one intrauterine viable fetus 10-11 weeks after transfer divided by number of embryos/blastocysts transferred. Preferably, the administration of an oxytocin receptor antagonist as disclosed herein increases the ongoing pregnancy rate by at least 5%, more preferably by at least 10% and most preferred by at least 20%.

"Implantation rate" as used herein refers to the number of intrauterine gestational sacs with fetal heart beat 5-6 weeks after transfer divided by number of embryos/blastocysts transferred. Preferably, the administration of an oxytocin receptor antagonist as disclosed herein increases the ongoing implantation rate by at least 5%, more preferably by at least 10% and most preferred by at least 20%.

"Clinical pregnancy rate" as used herein refers to a pregnancy with at least one intrauterine gestational sac with fetal heart beat 5-6 weeks after transfer divided by number of embryos/blastocysts transferred. Preferably, the administration of an oxytocin receptor antagonist as disclosed herein increases the clinical pregnancy rate by at least 5%, more preferably by at least 10% and most preferred by at least 20%.

"Live birth rate" refers to the number of live births per women treated. Preferably, the administration of an oxytocin receptor antagonist as disclosed herein increases the live birth rate by at least 5%, more preferably by at least 10% and most preferred by at least 20%.

"Therapeutically effective amount", as used herein, refers to an amount that produces the desired effect for which it is administered. In some embodiments, the term refers to an amount that is sufficient, when administered to a female subject undergoing embryo transfer in accordance with a therapeutic dosing regimen, to increase ongoing implantation rate, to increase ongoing pregnancy rate, to increase clinical pregnancy rate, and/or to increase live birth rate. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to female subjects in need of such treatment. Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

One aspect of the disclosure provides oxytocin receptor antagonists for use in increasing ongoing implantation rate, increasing ongoing pregnancy rate, increasing clinical pregnancy rate, and/or increasing live birth rate, relative to a control, in a female subject undergoing embryo transfer. Preferably, the ongoing implantation rate is increased relative to a control.

Previous large studies in the art report administration of oxytocin receptor antagonists in the early luteal phase (corresponding to day 2 or 3 post-retrieval) when uterine contraction frequency is high. The expectation was that these compounds, which reduce uterine contractility, would improve embryo implantation. However, the oxytocin receptor antagonists demonstrated no improved effects on implantation when provided in the early luteal phase (Ng et al. 2014). Thus, in certain embodiments, the present invention excludes immediate release or substantially immediate release formulations of oxytocin receptor antagonists administered in the early luteal phase (i.e., preceding the receptive endometrium stage).

The present disclosure demonstrates the effectiveness of oxytocin receptor antagonists on embryo implantation when provided after the early luteal phase, or rather, in the receptive endometrium stage and/or the when the embryo has reached the blastocyst-stage (see Example 1). Since the frequency of uterine contractions has returned or nearly returned to baseline at this stage, it was surprising and unexpected that a oxytocin receptor antagonist had an effect on the implantation rate.

Implantation is a critical process in which an embryo apposes, attaches and invades the endometrium. The uterus will accept the implanting embryo only during a limited period of time described as the "window of implantation" or "receptive window" (Makrigiannakis and Minas 2006; Strowitzki et al. 2006). The window of implantation is a period of a few days in which the endometrium acquires the receptive stage allowing embryo adhesion and invasion (Koot and Macklon 2013). This stage is referred to herein as the "receptive endometrium stage".

Successful implantation depends not only a receptive endometrium, but also on a functional embryo and the synchronized communication between the embryo and maternal tissues. Therefore, during the receptive window of implantation, the embryo also needs to be at the appropriate stage. Implantation occurs after a blastocyst hatches from the zona pellucida. Therefore, as is well known if the field of ART, if a blastocyst stage embryo is transferred, the woman should ideally be in the receptive endometrium stage, so that both the endometrium and the embryo are synchronized for implantation. If a cleavage stage embryo is transferred, then the woman should be in the pre-receptive stage. The endometrium and embryo will both further develop such that when the embryo reaches the blastocyst stage, the endometrium will have reached the receptive stage.

Accordingly, the antagonists disclosed herein are administered such that the effect of the antagonist overlaps with the receptive endometrium stage and/or the embryo reaching the blastocyst-stage. Preferably, the antagonists are provided such that the antagonist is released or continues to be released in the receptive endometrium stage and/or the embryo reaching the blastocyst-stage. As discussed further herein, the antagonists are usually formulated as immediate release compositions such that they are administered during the receptive endometrium stage. However, the disclosure also encompasses antagonists formulated as control or delayed release formulations, for example as a depot, such that they are administered during the pre-receptive stage, but are released during the receptive stage. Preferably, a therapeutically effective amount of the antagonist is present during at least a portion of the receptive endometrium stage of the female.

A number of cellular and morphological changes are associated with the transformation of a pre-receptive endometrium to a receptive endometrium. Biomarkers have also been identified which can be used to evaluate whether the endometrium is in a receptive stage. For example, the Endometrial Receptivity Array from Ignomix™ analyzes the expression of 238 genes in order to determine whether the endometrium is in the receptive stage (see, WO2010010201 and WO2010010213). Preferably, the receptive endometrium stage is defined as having a normal receptive profile based on the expression profile of one or more (e.g., all) of the 238 genes of the Endometrial Receptivity Array (ERA).

The receptive endometrium stage can also be characterized based on the stage of a normal ovulation cycle. Ovulation occurs after the luteinizing hormone (LH) surge, which normally takes place around day 14 of a normal ovulation cycle. The precise stage of the ovulation cycle can be characterized based on the timing of the LH surge. The LH surge can be measured by taking blood samples at various days of a woman's cycle. The day of the LH surge is considered as day LH 0. LH+1 then usually corresponds to day 15 of the cycle and LH+7 usually to day 21. The endometrium becomes receptive to implantation at around day LH+7 in natural cycles and remains receptive for usually about 4 days (Bergh and Navot 1992), although this timing varies for each woman. In preferred embodiments, the receptive endometrium stage corresponds to between day LH+6 and day LH+9 of a natural ovulation cycle, more preferably between LH+6 and LH+8. The receptive window lasts normally only 2-3 days per ovulation cycle. However, as is well-known in the art, there exists variability between women in both the length of the window and when it occurs.

In women undergoing oocyte retrieval for fresh embryo transfer, the receptive window can be characterized based on the day post-oocyte retrieval, the number of days in luteal phase support following oocyte retrieval, and/or the number of days following hCG administration.

In a typical IVF procedure, ovarian stimulation is used in order to stimulate the ovaries to produce multiple eggs. Gonadatropin releasing hormone (GnRH) agonists and GnRH antagonists can be given to prevent premature ovulation while human menopausal gonadotropin (hMG), follicle stimulating hormone (FSH), luteinizing hormone (LH), and clomiphene citrate can be given to stimulate the production of multiple eggs. Typically, eight to fourteen days of stimulation are required before the ovarian follicles are sufficiently developed. Human chorionic gonadotropin (hCG) is usually then administered to ensure the final stage of maturation and the eggs are retrieved prior to ovulation, usually around 36 hours after hCG administration. The day of hCG administration is defined as hCG+0 and oocyte retrieval is performed on hCG+2.

In preferred embodiments, the receptive endometrium stage corresponds to between day hCG+6 and day hCG+9 (or rather, 4 to 7 days post-oocyte retrieval), preferably between day hCG+6 and day hCG+8.

Egg retrieval is a minor surgical procedure that can be performed, for example, using transvaginal ultrasound aspiration. The eggs may be inspected microscopically and diagnosed to observe their morphological features. Insemination is then performed in vitro, for example by incubating oocytes together with sperm or by intracytoplasmic sperm injection (ICSI) in which sperm is injected with a microscopic needle into the egg. "Fertilization" refers to the penetration of the ovum by the spermatozoa and combination of their genetic material resulting in the formation of a zygote.

After fertilization, embryos are cultured in vitro. Methods for culturing and staging embryos are well-known in the art and are described in, e.g., US 20140134632, US 20140017717, US 20120252119, and US 20120252119, which are herein incorporated by reference in their entirety. Culture media known in the art that are suitable for use for the in vitro support of cell development and growth include human tubal fluid (HTF) (Irvine Scientific), N-2-hydroxyethylpiperazine-N'-2-ethane (HEPES) media (Irvine Scientific), IVF-50 (Scandanavian IVF Science), S2 (Scandanavian IVF Science), G1 and G2 (Scandanavian IVF Science), UnilVF, ISM-1, BlastAssist, UTM media (sold as MEDI-CULT® media by Origio A/S), Modified Whittens medium, Wittinghams T6 media, Ham's F-10 media, and Earle's solution. G1 and G2 media were specifically formulated to meet the physiological needs of the cleavage stage embryo and the embryo in the eight-cell through blastocyst stage of development. U.S. Pat. No. 6,605,468 discloses a medium for the propagation of early stage embryos to blastocyst stage.

Embryos may also be subjected to morphological, kinetic and/or genetic testing. Preferably, visual observation of the embryo by microscopy is used to determine if aberrant physical or morphological features are present (see, e.g., WO2013078312). Preimplantation genetic diagnosis is commonly performed to screen for inherited diseases. For this method, one or two cells are removed from an embryo to test for genetic diseases.

Methods of embryo transfer are well known in the art. One or more embryos may be aspirated into a catheter and inserted into the uterus, the uterine cavity or the fallopian tubes.

In some embodiments a cleavage-stage embryo is transferred. "Cleavage-stage" embryos range from 2-cells to 16 cells and can be characterized based on, e.g., fragmentation, symmetry of division, and absence of multinucleation (see Prados et al. Human Reproduction 2012 27:50-71 for review). Fragmentation is generally characterized by the percent of embryo volume that is replaced by fragments. Preferably, a cleavage-stage embryo is characterized as having 4 blastomeres on day 2 post-insemination and 6-8 blastomere on day 3 post-insemination. Preferably, the cleavage-stage embryo has at least 6 blastomeres and fragmentation of 20% or less.

Preferably, a day 2 or day 3 cleavage stage embryo is transferred. In fresh embryo transfers where the female has undergone oocyte retrieval, the day 2 or day 3 cleavage stage embryo is then usually transferred 2 or 3 days post-oocyte retrieval, respectively. The blastocyst stage of the embryo and the receptive endometrium stage are reached, ideally simultaneously, several days after transfer.

Preferably, a blastocyst-stage embryo is transferred. A "blastocyst-stage" embryo has an inner cell mass, an outer cell layer called the trophectoderm, and a fluid-filled blastocele cavity containing the inner cell mass from which the whole of the embryo is derived. An embryo normally reaches this stage at day 5 or 6 post-retrieval. A blastocyst-stage embryo can be characterized based on its expansion and hatching status. Expansion relates to the increasing volume of the cavity (i.e. blastocoel), while hatching refers to the herniation or escape of the blastocyst from its membrane (i.e. zona pellucida). The expansion and hatching status is characterized as follows:

1. An early blastocyst, blastocoel being less than half volume of that of the embryo
2. A blastocyst with a blastocoel whose volume is half of, or greater than half of, that of the embryo
3. A blastocyst with a blastocoel completely filling the embryo
4. An expanded blastocyst with a blastocoel volume larger than that of the early embryo, with a thinning zona
5. A hatching blastocyst with the trophectoderm starting to herniate through the zona
6. A hatched blastocyst, in which the blastocyst has completely escaped from the zona.

In preferred embodiments, the blastocyst-stage embryo for transfer has an expansion and hatching status of 3, 4, 5, or 6.

In fresh embryo transfers where the female has undergone oocyte retrieval, the blastocyst stage embryo is usually transferred to the female 5 or 6 days post-oocyte retrieval, preferably 5 days post-retrieval.

For women undergoing fresh embryo transfer following oocyte retrieval, the endometrium on day 2 and day 3 post-oocyte retrieval is typically in a pre-receptive stage and is not conducive to implantation. In preferred embodiments, the receptive endometrium stage corresponds to between day 4 and day 7 post-oocyte retrieval, preferably between day 5 and day 6. If hCG is used to induce ovulation or trigger final maturation, days 4 to 7 post-oocyte retrieval will normally correspond to hCG+6 to hCG+9.

Ovarian stimulation with fertility drugs usually leads to luteal phase deficiency. Therefore, it is generally standard practice for luteal phase support to be used in women following oocyte retrieval. Luteal phase support refers to therapeutic interventions during the luteal phase aiming at supplementing corpus luteal function for improving the embryo implantation and the early pregnancy development. Luteal phase support is known in the art and usually comprises supplementation with progesterone, estradiol and progesterone, progestins, hCG, and/or a GnRH agonist, or rather the administration of exogenous progesterone, estradiol and progesterone, progestins, hCG, and/or a GnRH agonist. Progesterone is normally administered intramuscularly or vaginally, while hCG is administered intra-muscularly or subcutaneously. Preferably, luteal phase support begins the first day after oocyte retrieval, i.e., day 1 post-oocyte retrieval.

Preferably, the receptive endometrium stage corresponds to between day 4 and day 7, preferably between day 4 and day 6, of luteal phase support in women who have undergone oocyte retrieval. In preferred embodiments, the female has undergone ovarian stimulation in preparation for oocyte retrieval.

The present disclosure encompasses the transfer of embryos into a female within a few days post fertilization (i.e., fresh embryo transfer), as well as the use of frozen embryos. Frozen embryo transfer (FET) is a known procedure that utilizes cryopreserved embryos from a previous cycle of in vitro fertilization or ICSI. The cryopreserved embryos are thawed and transferred into the uterine cavity through a catheter. The disclosure also encompasses the use of cryopreserved oocytes for fertilization. In these embodiments, oocytes can be later thawed, fertilized, and cultured and transferred as described herein.

Rapid freezing can be used for these purposes, for example together with a cryoprotectant. Conventional cryoprotectants include glycols such as ethylene glycol, propylene glycol, and glycerol; 2-methyl-2,4-pentanediol (MPD); dimethyl sulfoxide (DMSO) and sucrose. Alternatively, vitrification can also be used to freeze oocytes or embryos.

FET, as well as "third-party IVF" (gestational surrogacy, ovum donation, embryo donation), may be performed during a natural ovulation cycle. The receptive window for these women can be determined based on a natural ovulation cycle as described herein. In some embodiments, ovulation is induced with the administration of, e.g., hCG. Preferably, in these women the receptive window corresponds to between hCG+6 and hCG+9, preferably between hCG+6 and hCG+8.

In some embodiments, women undergoing FET or third party IVF also receive luteal support as described above. Preferably in these women the receptive window corresponds to between day 4 and day 9, preferably between day 5 and day 7, of luteal phase support. Luteal phase support is often used when FET or third party IVF is performed during an "artificial cycle". In these cases, the endometrium is prepared by administering estrogen and/or progesterone using methods known in the art. Preferably, luteal phase support begins after the endometrium is primed for at least 6 days with exogenous estrogen in order to induce an artificial cycle.

In an exemplary embodiment of FET or third party IVF, estrogen is provided orally or vaginally in doses of 4-8 mg daily for about 10 days, at which time luteal phase support is initiated with the administration of vaginal progesterone and blastocyst transfer occurs 6 days after starting progesterone.

In one embodiment of the disclosure, the effect of the oxytocin receptor antagonist overlaps with the blastocyst-stage of the embryo. Preferably, the antagonist is released when the embryo has reached the blastocyst-stage. Preferably, a blastocyst-stage embryo is transferred to said female and the antagonist is administered on the same day that the embryo is transferred. Preferably, a therapeutically effective amount of the antagonist is present during at least a portion of the blastocyst-stage of the transferred embryo.

The disclosure also contemplates the transfer of a cleavage-stage embryo. In these embodiments, the antagonist may be provided as a sustained or controlled release formulation for release several days after transfer. Alternatively, the antagonist may be administered as an immediate release formulation several days after transfer. As shown in the examples, administration of barusiban (an oxytocin receptor antagonist) when an embryo is in the blastocyst-stage results in an increase in ongoing implantation rate from 27% to 45%, a significant increase.

Oxytocin receptor antagonists are known in the art, and any oxytocin receptor antagonist can be used in the methods of the disclosure. Preferably, the oxytocin receptor antagonists are selected from selective oxytocin antagonists and mixed vasopressin/oxytocin receptor antagonists. A selective oxytocin antagonist has a Ki for the oxytocin receptor which is at least one order of magnitude higher than the Ki for the vasopressin receptor.

Receptor antagonists include compounds which reduce the expression and/or activity of an oxytocin receptor. A preferred vasopressin/oxytocin receptor antagonist is atosiban (1-(3-mercaptopropanoic acid)-2-(O-ethyl-D-tyrosine)-4-L-threonine-8-L-ornithine-oxytocin).

Oxytocin receptor antagonists also include RNA interference or RNA antisense molecules directed against said receptor.

Preferably, the antagonist binds to the receptor and prevents receptor activity. Such antagonists include, e.g., antibodies directed against the receptor (e.g., "neutralizing antibodies") as well as small molecules. Preferably, the antagonist acts as a competitive antagonist and competes with oxytocin for binding to the oxytocin receptor. Preferably, the antagonists are small molecules that bind to the receptor and antagonize receptor activity. A preferred selective oxytocin antagonist is barusiban.

Suitable oxytocin receptor antagonists are well-known to the skilled person and can be easily identified based on known screening methods which use, e.g., receptor activation and/or receptor binding as a read-out. Suitable antagonists include those disclosed in U.S. Pat. No. 6,143,722, which is hereby incorporated by reference in its entirety. U.S. Pat. No. 6,143,722 discloses heptapeptide analogues, or a pharmaceutically acceptable salts thereof, having oxytocin antagonist activity and consisting of a hexapeptide moiety S and a C-terminal beta-aminoalcohol residue Z bound to the moiety S by an amide bond, wherein the beta-aminoalcohol Z is:

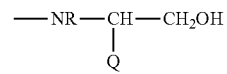

wherein Q is (CH2)n-NH-A, n is 1-6 and A is H or —C(=NH) NH2, and wherein R is CH3 or C2H5;
and the moiety S is:

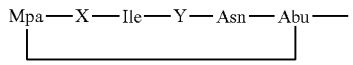

wherein Mpa, Ile, Asn and Abu have the following meaning:
Mpa 3 mercaptopropionic acid residue
Ile isoleucine residue
Asn asparagine residue
Abu alpha-aminobutyric acid residue;
and wherein X is a D-aromatic alpha-amino acid; and Y is an aliphatic alpha-amino acid. Preferred oxytocin antagonists are listed in FIG. 1.

Further antagonists include OBE001/AS-602305 (in particular oral formulations thereof), TT-235 (Northwestern University), the selective oxytocin receptor antagonist Epelsiban ((3R,6R)-3-(2,3-dihydro-1H-inden-2-yl)-1-[(1R)-1-(2,6-dimethylpyridin-3-yl)-2-(morpholin-4-yl)-2-oxoethyl]-6-[(1S)-1-methylpropyl]piperazine-2,5-dione); Retosiban ((3R,6R)-6-[(2S)-butan-2-yl]-3-(2,3-dihydro-1H-inden-2-yl)-1-[(1R)-1-(2-methyl-1,3-oxazol-4-yl)-2-(morpholin-4-yl)-2-oxoethyl]piperazine-2,5-dione); PF-3274167 (5-(3-(3-(2-chloro-4-fluorophenoxy)azetidin-1-yl)-5-(methoxymethyl)-4H-1,2,4-triazol-4-yl)-2-methoxypyridine); and L-368,899 hydrochloride (CAS 148927-60-0); L-371,257 (1-[1-[4-(1-acetylpiperidin-4-yl)oxy-2-methoxybenzoyl]piperidin-4-yl]-4H-3,1-benzoxazin-2-one). Additional oxytocin antagonists are also described, e.g., in WO2004020414 and WO2005/028452, which are hereby incorporated by reference in their entirety. Preferably, the antagonist is selected from barusiban, atosiban, OBE001/AS-602305, PF-3274167 Epelsiban, and retosiban.

Preferably, the oxytoxin receptor antagonist is formulated in a pharmaceutical composition. The composition may also include pharmaceutically acceptable additives such as preservatives, diluents, dispersing agents, agents to promote mucosal absorption (examples of which are disclosed by Merkus, F. W. H. M. et al., J. Controlled Release 24, 201-208, 1993, and which include surfactants, bile acids, fusidates, phospholipids and cyclodextrins), buffering agents and flavourings. Such compositions may be formulated as solids (for example as tablets, capsules or powders) or liquids (for example as solutions or suspensions), which is here taken to include creams and ointments, for oral or parenteral administration. Oral (including sublingual and buccal), intranasal, pulmonary, transdermal, rectal, vaginal, subcutaneous, intramuscular and intravenous administration may all be suitable routes for dosing.

In some embodiments, the pharmaceutical composition can be delivered in a sustained or delayed release system. For example, the antagonist may be administered using a transdermal patch or formulated in lipophilic depots (e.g. fatty acids, waxes, oils). As used herein, a sustained or delayed release system ensures that the antagonist is also present in the subject at a time point after administration, e.g., several hours or even several days after administration. Such sustained or delayed release systems allow the administration of the receptor antagonists before the female is in a receptive endometrium stage. The sustained or delayed release, however, ensures that a sufficient amount (or rather a therapeutically effective amount) of the antagonist is still present when the female enters the receptive endometrium stage and/or when the embryo has reached the blastocyst-stage.

In embodiments where the female is undergoing transfer of a cleavage-stage embryo, the antagonist should be released when the cleavage-stage embryo has developed into a blastocyst-stage embryo and/or when the female has reached the receptive endometrium stage. If an immediate release formulation is used, then the antagonist should be administered several days after embryo transfer, preferably two or three days after embryo transfer as this will correspond to the time when the cleavage-stage embryo has developed into a blastocyst-stage embryo and/or when the female has reached the receptive endometrium stage. If sustained or delayed release formulations are used, these may be administered earlier, for example on the day of embryo transfer, provided that the antagonist is released when the cleavage-stage embryo has developed into a blastocyst-stage embryo and/or when the female has reached the receptive endometrium stage.

In embodiments where the female is undergoing transfer of a blastocyst-stage embryo, the antagonist should be released on the same day as embryo transfer (e.g., within the same 24 hour period), as this will correspond to the time when the embryo has reached the blastocyst-stage and the female has reached the receptive endometrium stage. Preferably, the antagonist is administered between 2 hours prior to and 2 hours post embryo transfer. More preferably, the antagonist is administered twice. In an exemplary embodiment using barusiban, the first administration may take place around 45 minutes prior to embryo transfer and the second administration around 60 minutes after the first administration.

As is well-known to a skilled person, the timing of administration is dependent of the particular antagonist used, in particular on the half-life of the antagonist. Antagonists with relatively short half-lives may need to be administered multiple times in order to ensure that their effects overlap the blastocyst-stage and/or the receptive endometrium stage.

REFERENCES

Ayoubi J-M, Epiney M, Brioschi P A, Fanchin R, Chardonnens D, de Ziegler D. Comparison of changes in uterine contraction frequency after ovulation in the menstrual cycle and in in vitro fertilization cycles. Fertil Steril 2003; 79: 1101-1105.

Bergh P A, Navot D. The impact of embryonic development and endometrial maturity on the timing of implantation. Fertil Steril 1992; 58: 537-542.

Bernabeu R, Roca M, Tones A, Ten J. Indomethacin effect on implantation rates in oocyte recipients. Hum Reprod 2006; 21: 364-369.

Blockeel C, Pierson R, Popovic-Todorovic B, Visnova H, Garcia-Velasco J A, Mrázek M, Chou P-Y, Wu M-H, Pan H-A, Hung K-H, Chang F-M. Use of an oxytocin antagonist in in vitro fertilization-embryo transfer for women with repeated implantation failure: a retrospective study. Taiwan J Obstet Gynecol 2011; 40: 136-140.

Fanchin R, Righini C, Olivennes F, Taylor S, de Ziegler D, Frydman R. Uterine contractions at the time of embryo transfer alter pregnancy rates after in-vitro fertilization. Hum Reprod 1998; 13: 1968-1974.

Fanchin R, Righini C, de Ziegler D, Olivennes F, Ledée N, Frydman R. Effects of vaginal progesterone administration on uterine contractility at the time of embryo transfer. Fertil Steril 2001; 75: 1136-1140.

Fuchs A-R, Behrens O, Maschek H, Kupsch E, Einspanier A. Oxytocin and vasopressin receptors in human and uterine myomas during menstrual cycle and early pregnancy. Hum Reprod Update 1998; 4: 594-604.

Killick S R. Ultrasound and the receptivity of the myometrium. RBM Online 2007; 15: 63-67.

Kim C H, Lee J W, Jeon I K, Park E, Lee Y J, Kim S H, Chae H, Kang B M, Lee H A. Administration of oxytocin antagonist improves the implantation rates in patients with repeated failure of IVF/ICSI treatment. Hum Reprod 2008; 23 (Suppl. 1): i124.

Koot Y E M, Macklon N S. Embryo implantation: biology, evaluation, and enhancement. Curr Opin Obstet Gynecol 2013; 25: 274-279.

Lan V T, Khang V N, Nhu G H, Thuong H M. Atosiban improves implantation and pregnancy rates in patients with repeated implantation failure. RBM Online 2012; 25: 254-260.

Lesny P, Killick S R, Tetlow R L, Robinson J, Maguiness S D. Embryo transfer—can we learn anything new from the observation of junctional zone contractions? Hum Reprod 1998; 13: 1540-1546.

Liang Y L, Kuo T C, Hung K H, Chen T H, Wu M H. Oxytocin antagonist for repeated implantation failure and delay of delivery. Taiwan J Obstet Gynecol 2009; 48: 314-316.

Makrigiannakis A, Minas V. Mechanisms of implantation. RBM Online 2006; 14: 102-109.

Moon H S, Park S H, Lee J O, Kim K S, Joo B S. Treatment with piroxicam before embryo transfer increases the pregnancy rate after in vitro fertilization and embryo transfer. Fertil Steril 2004; 82: 816-820.

Moraloglu O, Tonguc E, Turgut V, Zeyrek T, Batioglu S. Treatment with oxytocin antagonists before embryo transfer may increase implantation rates after IVF. RBM Online 2010; 21: 338-343.

Ng E H, Li R H, Chen L, Lan V T, Tuong H M, Quan S. A randomized double blind comparison of atosiban in patients undergoing IVF treatment. Hum Reprod 2014; 29: 2687-2694.

Papanikolaou E G, Kolibianakis E M, Tournaye H, Venetis C A, Fatemi H, Tarlatzis B and Devroey P. Live birth rates after transfer of equal number of blastocysts or cleavage-stage embryos in IVF. A systematic review and meta-analysis. Hum Reprod 2008; 23: 91-99.

Pierzynski P, Reinheimer T M, Kuczynski W. Oxytocin antagonists may improve infertility treatment. Fertil Steril 2007; 88: e19-e22.

Richter O N, Bartz C, Dowaji J, Kupka M, Reinsberg J, Ulrich U, Rath W. Contractile reactivity of human myometrium in isolated non-pregnant uteri. Hum Reprod 2006; 21: 36-45.

Schoolcraft W B, Surrey E S, Gardner D K. Embryo transfer: techniques and variables affecting success. Fertil Steril 2001; 76: 863-870.

Simón C, Martin J C, Pellicer A. Paracrine regulators of implantation. Clin Obstet Gynaecol 2000; 14: 815-826.

Shukovski L, Healy D L, Findlay J K. Circulating immunoreactive oxytocin during the human menstrual cycle comes from the pituitary and is estradiol dependent. J Clin Endocrinol Metab 1989; 68: 455-460.

Strowitzki T, Germeyer A, Popovici R, Wolff M. The human endometrium as a fertility-determining factor. Hum Reprod Update 2006; 12: 617-630.

Zhu L, Che H S, Xiao L, Li Y P. Uterine peristalsis before embryo transfer affects the chance of clinical pregnancy in fresh and frozen-thawed embryo transfer cycles. Hum Reprod 2014; 29: 1238-1243.

All patent and literature references cited in the present specification are hereby incorporated by reference in their entirety.

The invention is further explained in the following examples. These examples do not limit the scope of the invention, but merely serve to clarify the invention.

EXAMPLES

Example 1

A randomized, placebo-controlled, double-blind, parallel groups, multinational, multicenter trial assessing the effect of barusiban administered subcutaneously on the day of transfer on implantation and pregnancy rates in IVF/ICSI patients Methodology BASIC was a randomized, double-blind, placebo-controlled, parallel groups, multinational, multicenter trial. It was designed to evaluate the effects of barusiban, administered either on the day of cleavage-stage embryo transfer or on the day of blastocyst transfer, on ongoing implantation rate in IVF/ICSI patients. The patients underwent controlled ovarian stimulation in the long GnRH agonist or GnRH antagonist protocol, received hCG for triggering of final follicular maturation, had undergone oocyte retrieval, and had daily luteal phase support by supplementation with vaginal progesterone starting on day 1 post-retrieval, and transfer on day 3 or 5 post-retrieval. Patients were randomized in a 1:1 ratio to either the barusiban group or the placebo group, with stratification according to the day of transfer (day 3 post-retrieval or day 5 post-retrieval) and the number of embryos/blastocysts to be transferred (1 or 2). In total, 255 IVF/ICSI patients were randomized in the trial and contributing with 440 embryos/blastocysts.

Investigational medicinal product, i.e., barusiban or placebo according to randomization, was administered as subcutaneous injections at two time points: 1st administration of 40 mg barusiban or placebo was 45 min prior to transfer and the 2nd administration of 10 mg barusiban or placebo was 60 min after the 1st administration.

Transfer was performed on day 3 (cleavage-stage embryos) or day 5 (blastocysts) after oocyte retrieval. On day 3, only embryos of good quality defined as ≥6 blastomeres and ≤20% fragmentation were transferred. On day 5, blastocysts with expansion and hatching status 3, 4, 5 or 6 were transferred. The actual number of transferred embryos/blastocysts for each individual patient depended on the availability of embryos/blastocysts of the required morphological quality, local regulations and clinical practice for the patient's age, but the maximum number was 2.

Key aspects related to the transfer procedure had been standardized. A speculum was inserted into the vagina and cleaning of the vagina and cervix was done according to local practices but with minimal manipulation and disturbance. Soft or ultrasoft catheters were used. The outer sheath of the catheter was inserted just protruding to the internal os (i.e. keeping the outer sheath in the cervical canal). The embryo(s)/blastocyst(s) were loaded into the inner sheath which was then inserted through the outer sheath. Using abdominal ultrasound guidance, the embryo(s)/blastocyst(s) were placed 1.5-2.0 cm from the fundus. The time from loading the inner catheter to placing the embryo(s)/blastocyst(s) should not have exceeded 1 min. After placement, the inner and outer catheters were withdrawn and checked for retained embryo(s)/blastocyst(s), mucus and blood. After confirmation that there were no embryo(s)/blastocyst(s) left in the catheters, the speculum was subsequently removed; this occurred approximately within 2 min after placement of the embryo(s)/blastocyst(s). Any difficulties/eventualities occurring during the transfer procedure were recorded.

Patients received vaginal progesterone tablets 100 mg twice daily from the day after oocyte retrieval and until the day of the clinical pregnancy visit. On the day of transfer, patients should insert the progesterone tablets at least 3 hours before transfer and at least 3 hours after transfer. Ongoing implantation rate (primary endpoint) was defined as the number of intrauterine viable fetuses 10-11 weeks after transfer divided by number of embryos/blastocysts transferred.

With respect to statistical methodology, the primary hypothesis was tested using a logistic regression model with ongoing implantation (yes/no) as the outcome and treatment and randomization strata as factors. The treatment effect is presented on the odds ratio scale, as this represents the outcome of the logistic regression analysis; an analysis that allows for inclusion of factors and co-variates. It must be stressed that the odds ratio based on the logistic regression model provides the most appropriate way of representing the data and the basis for evaluation of treatment effect.

Several factors impact the probability of a successful outcome of an embryo transfer, including the day of transfer, the number of embryos/blastocyst transferred, and the quality of the embryo/blastocyst transferred. The randomization was stratified for the first two of these factors ensuring comparable groups. However, as the embryos develop continuously it was not feasible to stratify for the quality of the transferred embryo/blastocyst. Instead, adjustment for the quality of the embryo/blastocyst was included in the primary analysis.

Results

The impact of treatment on the different receptivity stages and implantation potential of cleavage-stage embryos and blastocysts was apparent, as illustrated by overall ongoing implantation rates of 19% for day 3 post-retrieval transfers and 38% for day 5 post-retrieval transfers. The same pattern was observed in both the barusiban and placebo groups.

Figure 3:
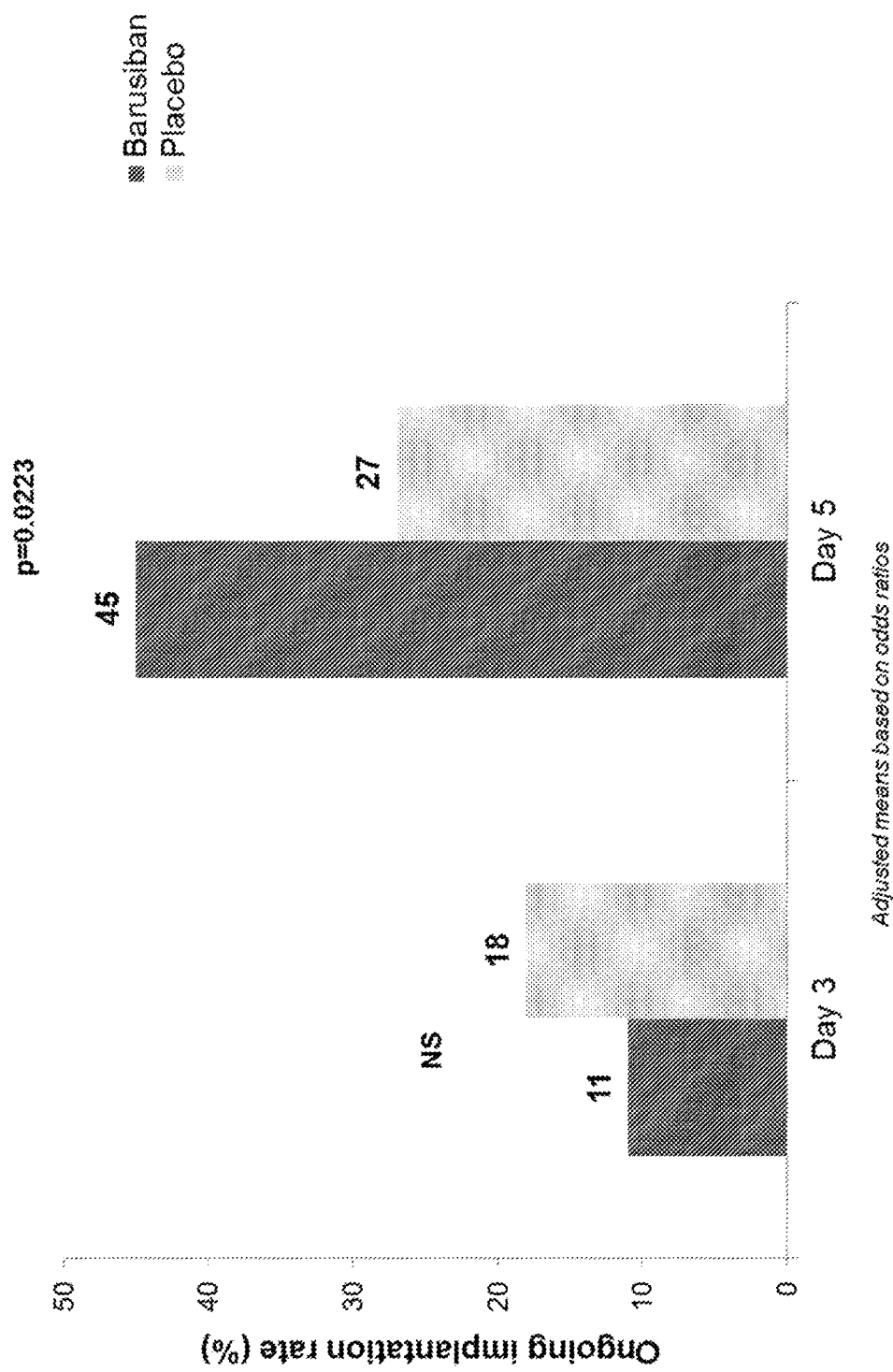
FIG. 3 is a graph of ongoing implantation rate by day of transfer for (BASIC) clinical trial.

The observed overall (day 3+day 5) ongoing implantation rate in the trial was 27.1% for barusiban and 28.2%[1], corresponding to an odds ratio[2] of 1.1 (95% confidence interval 0.7-1.8; p=0.6960), i.e., in favor of barusiban but not significant. Therefore, the primary endpoint for the overall trial population was not met, but as described below this was because the day of transfer had an interaction. Transfer of cleavage-stage embryos on day 3 post-retrieval yielded an odds ratio of 0.3 (0.3-1.2; p=0.1509) (FIG. 2). Analysis of the day 5 post-retrieval strata resulted in an odds ratio of 2.3 (1.1-4.7; p=0.0270) and thereby demonstrated a significant treatment effect of barusiban on ongoing implantation rate for blastocyst transfers (FIG. 2). An odds ratio of 2.3 corresponds to adjusted means of ongoing implantation rates for blastocyst transfers of 45% for barusiban vs 27% for placebo (relative Δ of 67%) (FIG. 3).

[1] Data presented in this document are for the per-protocol (PP) population. Similar results were observed for the intention-to-treat (ITT) population. For example, the ongoing implantation rate for the ITT population was 26.2% for barusiban and 27.9% for placebo.
[2] The odds ratios are based on the logistic regression model, for which the analyses are adjusted for site, primary reason for infertility and embryo/blastocyst quality.

The results from the BASIC trial indicated that interpretation of the effects of an oxytocin antagonist on implantation rate was affected by day of transfer; cleavage-stage embryo transfer (day 3 post-retrieval) or blastocyst transfer (day 5 post-retrieval). No effect on ongoing implantation rate was established for barusiban when cleavage-stage embryo transfer was done on day 3 (pre-receptive stage). However, a significant (p=0.0270) effect of barusiban on improving ongoing implantation rate was observed when blastocyst transfer was done on day 5 (receptive stage).

The BASIC trial identified the time window for a clinically relevant impact of barusiban, or generally for oxytocin antagonists and mixed oxytocin/vasopressin antagonists, on implantation, which was not predicted in advance of the trial. An effect on implantation rate is seen when the oxytocin antagonist is administered at the time of implantation, on day 5 post-retrieval (or later), but not in the early luteal phase on day 2-3 post-retrieval.

The lack of a consistent effect between day 3 post-retrieval cleavage-stage embryo transfers and day 5 post-retrieval blastocyst transfers is of importance for the hypotheses on the mechanisms related to uterine contractility and consequences for cycle outcome. For both days, the dose and method of administration of pharmacological intervention as well as the transfer procedure were the same. Therefore, the mechanisms proposed such as expulsion or dispersion of embryos/blastocysts due to uterine contractility in the early luteal phase or due to the embryo/blastocyst transfer procedure should no longer be considered potential explanations for improvement of implantation rates with utero-relaxant agents, including oxytocin antagonists or mixed oxytocin/vasopressin antagonists. In case these mechanisms were the most relevant, the findings should have been the same for day 3 and day 5 post-retrieval observations.

The invention claimed is:

1. A method of treating a female subject undergoing embryo transfer, comprising
   administering to the female subject an OBE001 oxytocin receptor antagonist:
   (1) only during a time
      a) between day 6 following luteinizing hormone (LH) surge (LH+6) and day 9 following LH surge (LH+9) of a natural ovulation cycle;
      b) between day 6 following human chorionic gonadotropin (hCG) administration (hCG+6) and day 9 following hCG administration (hCG+9) of an induced ovulation cycle;
      c) between day 6 and day 7 of a luteal phase support following oocyte retrieval; or
      d) between day 6 and day 9 of a luteal phase support; or
   (2) only on the day of transfer of an embryo, wherein the transferred embryo is a blastocyst-stage embryo.

2. The method of claim 1, wherein the transferred embryo is a blastocyst-stage embryo.

3. The method of claim 2, wherein the blastocyst-stage embryo has an expansion and hatching status of 3, 4, 5, or 6.

4. The method of claim 1, wherein the antagonist is administered to the female subject on the same day as embryo transfer.

5. The method of claim 1, wherein the antagonist is administered orally.

6. The method of claim 1, further comprising transferring an embryo into the uterus, the uterine cavity, or the fallopian tubes of the female subject.

7. The method of claim 1, wherein the antagonist is administered to the female subject between 2 hours prior to and 2 hours after embryo transfer.

8. The method of claim 1, wherein the antagonist is administered to the female subject at day 5 post oocyte retrieval.

9. The method of claim 1, further comprising administering luteal phase support to the female subject.

10. The method of claim 9, wherein the luteal phase support comprises supplementation with progesterone, estradiol and progesterone, human chorionic gonadotropin, a progestin and/or a gonadatropin releasing hormone (GnRH) agonist.

11. The method of claim 1, wherein the transferred embryo is a cleavage-stage embryo and the antagonist is administered to the female subject only during a time a) between day 6 following luteinizing hormone (LH) surge (LH+6) and day 9 following LH surge (LH+9) of a natural ovulation cycle; b) between day 6 following human chorionic gonadotropin (hCG) administration (hCG+6) and day 9 following hCG administration (hCG+9) of an induced ovulation cycle; c) between day 6 and day 7 of a luteal phase support following oocyte retrieval; or d) between day 6 and day 9 of a luteal phase support.

12. The method of claim 11, wherein the cleavage-stage embryo is a day 2 or day 3 post-fertilization embryo.

13. A method of implanting an embryo in a female subject, said method comprising transferring an embryo into the uterus, the uterine cavity or the fallopian tubes of a female subject and administering to the female subject an OBE001 oxytocin receptor antagonist:
(1) only during a time
a) between day 6 following luteinizing hormone (LH) surge (LH+6) and day 9 following LH surge (LH+9) of a natural ovulation cycle;
b) between day 6 following human chorionic gonadotropin (hCG) administration (hCG+6) and day 9 following hCG administration (hCG+9) of an induced ovulation cycle;
c) between day 6 and day 7 of a luteal phase support following oocyte retrieval; or
d) between day 6 and day 9 of a luteal phase support; or
(2) only on the day of transfer of an embryo, wherein the transferred embryo is a blastocyst-stage embryo.

14. The method of claim 13, wherein the antagonist is administered to the female subject at day 5 post oocyte retrieval.

15. The method of claim 13, wherein the luteal phase support comprises supplementation with progesterone, estradiol and progesterone, human chorionic gonadotropin, a progestin and/or a gonadatropin releasing hormone (GnRH) agonist.

16. The method of claim 13, wherein the transferred embryo is a cleavage-stage embryo and the antagonist is administered to the female subject only during a time a) between day 6 following luteinizing hormone (LH) surge (LH+6) and day 9 following LH surge (LH+9) of a natural ovulation cycle; b) between day 6 following human chorionic gonadotropin (hCG) administration (hCG+6) and day 9 following hCG administration (hCG+9) of an induced ovulation cycle; c) between day 6 and day 7 of a luteal phase support following oocyte retrieval; or d) between day 6 and day 9 of a luteal phase support.

17. The method of claim 13, wherein the transferred embryo is a blastocyst-stage embryo, and wherein the antagonist is administered to the female subject on the same day as embryo transfer.

18. A method of treating a female subject undergoing embryo transfer, comprising: administering to the female subject (i) luteal phase support comprising progesterone, and (ii) an OBE001 oxytocin receptor antagonist on the same day a blastocyst-stage embryo is transferred to the female subject.

* * * * *